United States Patent
Eckhardt et al.

(10) Patent No.: US 7,179,809 B2
(45) Date of Patent: Feb. 20, 2007

(54) 2-AMINO-IMIDAZO[4,5-D]PYRIDAZIN-4-ONES, THEIR PREPARATION AND THEIR USE AS PHARMACEUTICAL COMPOSITIONS

(75) Inventors: Matthias Eckhardt, Biberach (DE); Frank Himmelsbach, Mittelbiberach (DE); Elke Langkopf, Warthausen (DE); Norbert Hauel, Schemmerhofen (DE); Mohammad Tadayyon, Ulm (DE); Leo Thomas, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/102,048

(22) Filed: Apr. 8, 2005

(65) Prior Publication Data

US 2005/0234235 A1    Oct. 20, 2005

Related U.S. Application Data

(60) Provisional application No. 60/582,265, filed on Jun. 23, 2004, provisional application No. 60/568,137, filed on May 5, 2004.

(30) Foreign Application Priority Data

Apr. 10, 2004 (DE) .................. 10 2004 017 739
May 25, 2004 (DE) .................. 10 2004 025 552

(51) Int. Cl.
*C07D 471/04* (2006.01)
*A61K 31/5025* (2006.01)

(52) U.S. Cl. .............. 514/248; 544/118; 544/236; 514/234.2

(58) Field of Classification Search ............... 544/236, 544/118; 514/248, 234.2
See application file for complete search history.

(56) References Cited

U.S. PATENT DOCUMENTS

| 2004/0116328 A1 | 6/2004 | Yoshikawa et al. |
| 2005/0020574 A1 | 1/2005 | Hauel et al. |
| 2005/0026921 A1 | 2/2005 | Eckhardt et al. |

FOREIGN PATENT DOCUMENTS

| WO | WO 03/104229 A1 | 12/2003 |
| WO | WO 2004/050658 A1 | 6/2004 |
| WO | WO 2004/111051 A1 | 12/2004 |

*Primary Examiner*—Kahsay Habte
(74) *Attorney, Agent, or Firm*—Michael P. Morris; Mary-Ellen M. Devlin; Thomas Blankinship

(57) ABSTRACT

The present invention relates to 2-amino-imidazo[4,5-d]pyridazin-4-ones and 2-amino-imidazo[4,5-c]pyridin-4-ones of general formula

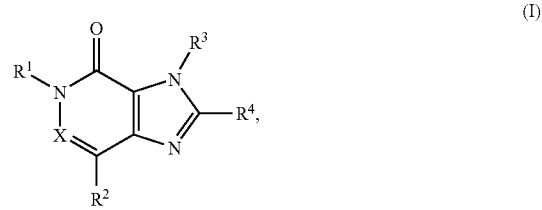

(I)

wherein $R^1$ to $R^4$ and X are defined as in claims 1 to 6, the tautomers, the enantiomers, the diastereomers, the mixtures thereof and the salts thereof, which have valuable pharmacological properties, particularly an inhibiting effect on the activity of the enzyme dipeptidylpeptidase-IV (DPP-IV).

10 Claims, No Drawings

2-AMINO-IMIDAZO[4,5-D]PYRIDAZIN-4-ONES, THEIR PREPARATION AND THEIR USE AS PHARMACEUTICAL COMPOSITIONS

This case claims the benefit under 35 U.S.C. 119(a) of German Patent Applications 102 004 017 739 (filed Apr. 10, 2004) and 102 004 025 552 (filed May 25, 2004), which foreign priority applications are hereby incorporated herein by reference in their entirties. This application also claims the benefit under 35 U.S.C. 119(e) of U.S. Provisional Patent Applications 60/568,137 (filed May 5, 2004) and 60/582,265 (filed Jun. 23, 2004), which domestic priority applications are hereby incorporated herein by reference in their entirties.

The present invention relates to new substituted imidazo[4,5-d]pyridazin-4-ones and 2-amino-imidazo[4,5-c]pyridin-4-ones of general formula I:

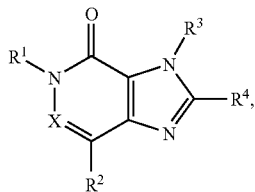

(I)

the tautomers, enantiomers, diastereomers, salts, particularly physiologically acceptable salts with inorganic or organic acids, and mixtures thereof, which have valuable pharmacological properties, such as an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, such as type I or type II diabetes mellitus, the pharmaceutical compositions containing a compound of general formula (I) or a physiologically acceptable salt thereof, and processes for the preparation thereof.

Imidazo[4,5-d]pyridazin-4-ones and imidazo[4,5-c]pyridin-4-ones which are substituted bicyclic groups in the 2 position are known from WO 03/104229.

In the above formula I
$R^1$ denotes:
  an arylmethyl or arylethyl group,
  a heteroarylmethyl or heteroarylethyl group,
  an arylcarbonylmethyl group,
  a heteroarylcarbonylmethyl group, or
  an arylprop-2-enyl or heteroarylprop-2-enyl group, wherein the propenyl chain may be substituted by 1 to 4 fluorine atoms or a cyano, $C_{1-3}$-alkyloxy-carbonyl or nitro group,
X denotes a nitrogen atom or a C—$R^5$ group, while $R^5$ denotes a hydrogen atom or a $C_{1-3}$-alkyl group,
$R^2$ denotes
  a hydrogen atom,
  a $C_{1-6}$-alkyl group,
  an aryl or heteroaryl group,
  a $C_{1-6}$-alkyl group substituted by a group $R_a$, where $R_a$ denotes
    a $C_{3-7}$-cycloalkyl group, wherein one or two methylene groups may each be replaced independently of one another by an oxygen or sulphur atom, by an —NH— or —N($C_{1-3}$-alkyl)- group, or by a carbonyl, sulphinyl or sulphonyl group, or a trifluoromethyl, aryl, heteroaryl, cyano, carboxy, $C_{1-3}$-alkoxy-carbonyl, aminocarbonyl, $C_{13}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, arylcarbonyl, heteroarylcarbonyl, $C_{1-3}$-alkylsulphinyl, $C_{1-3}$-alkylsulphonyl, hydroxy, $C_{1-3}$-alkoxy, $C_{1-3}$-alkylsulphanyl, amino, $C_{1-3}$-alkylamino, di-($C_{1-3}$-alkyl)-amino, pyrrolidin-1-yl, piperidin-1-yl, morpholin-4-yl, piperazin-1-yl, or 4-($C_{1-3}$-alkyl)-piperazin-1-yl group,
  a trifluoromethyl, carboxy, $C_{1-4}$-alkoxy-carbonyl, aminocarbonyl, $C_{1-3}$-alkyl-amino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, arylcarbonyl, heteroarylcarbonyl, $C_{1-3}$-alkylsulphinyl, $C_{1-3}$-alkylsulphonyl, $C^{1-4}$-alkoxy, $C_{1-4}$-alkylsulphanyl, amino, $C_{1-3}$-alkylamino or di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group,
  a $C_{3-7}$-cycloalkyl group wherein one or two methylene groups independently of one another may each be replaced by an oxygen or sulphur atom, by an —NH— or —N($C_{1-3}$-alkyl)- group, or by a carbonyl, sulphinyl or sulphonyl group, or
  a $C_{3-6}$-alkenyl or $C_{3-6}$-alkynyl group,
$R^3$ denotes
  a $C_{5-7}$-cycloalkenylmethyl group optionally substituted by a $C_{1-3}$-alkyl group,
  an arylmethyl or heteroarylmethyl group,
  a straight-chain or branched $C_{2-8}$-alkenyl group which may be substituted by 1 to 15 fluorine atoms or a cyano, nitro or $C_{1-3}$-alkoxy-carbonyl group,
  or a straight-chain or branched $C_{3-8}$-alkynyl group which may be substituted by 1 to 9 fluorine atoms or a cyano, nitro or $C_{1-3}$-alkoxy-carbonyl group,
and
$R^4$ denotes
  an amino group substituted by the groups $R^{15}$ and $R^{16}$ wherein
    $R^{15}$ denotes
      a hydrogen atom, a $C_{1-6}$-alkyl, $C_{3-6}$-cycloalkyl, $C_{3-6}$-cycloalkyl-$C_{1-3}$-alkyl, aryl or aryl-$C_{1-3}$-alkyl group and
    $R^{16}$ denotes
      a $R^{17}$—$C_{2-3}$-alkyl group, while the $C_{2-3}$-alkyl moiety is straight-chain and may be substituted by 1 to 4 $C_{1-3}$-alkyl groups; which may be identical or different, and the $C_{2-3}$-alkyl group may be linked to $R^{17}$ from position 2 onwards, and
      $R^{17}$ denotes an amino or $C_{1-3}$-alkylamino group,
  an amino group substituted by the groups $R^{15}$ and $R^{18}$ wherein
    $R^{15}$ is as hereinbefore defined and $R^{18}$ denotes a $C_{3-10}$-cycloalkyl-$C_{1-2}$-alkyl- group substituted in the 1 position of the cycloalkyl group by $R^{19}$ or a $C_{3-10}$-cycloalkyl group substituted in 1 or 2 position by a $R^{19}$—$C_{1-2}$-alkyl- group, while $R^{19}$ denotes an amino or $C_{1-3}$-alkylamino group, an amino group substituted by the groups $R^{15}$ and $R^{20}$ wherein $R^{15}$ is as hereinbefore defined and $R^{20}$ denotes a $C_4$— or $C_{8-10}$-cycloalkyl group wherein a methylene group is replaced by an —NH— group from position 3 onwards of the $C_4$— or $C_{8-10}$-cycloalkyl group, or an amino group substituted by the groups $R^{15}$ and $R^{21}$ wherein $R^{15}$ is as hereinbefore defined and $R^{21}$ denotes a $C_{3-4}$ or $C_{8-10}$-cycloalkyl group substituted in the 2 or 3 position by an amino or $C_{1-3}$-alkylamino group, while the above-mentioned groups $R^{18}$, $R^{20}$, and $R^{21}$ may be mono- or disubstituted by $R_b$, the substituents may be identical or different, and $R_b$ denotes a fluorine atom, a $C_{1-3}$-alkyl, trifluoromethyl, cyano, amino, $C_{1-3}$-alkylamino, hydroxy or $C_{1-3}$-alkyloxy group, and wherein one or two methylene groups of the cycloalkyl group independently of one another may each be replaced by an oxygen or sulphur atom or by an —NH— or —N($C_{1-3}$-alkyl)- group, or by a carbonyl, sulphinyl, or sulphonyl group.

By the aryl groups mentioned in the definition of the above groups is meant phenyl or naphthyl groups, which may be mono-, di-, or trisubstituted independently of one another by $R_h$, while the substituents may be identical or different, and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, morpholinyl, hydroxy, $C_{1-3}$-alkyloxy, difluoromethoxy, or trifluoromethoxy group, and additionally wherein each hydrogen atom may be replaced by a fluorine atom.

By the heteroaryl groups mentioned in the definition of the above-mentioned groups is meant:

a pyrrolyl, furanyl, thienyl, pyridyl, indolyl, benzofuranyl, benzothiophenyl, quinolinyl, or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, and the above-mentioned heteroaryl groups may be mono- or disubstituted by $R_h$, while the substituents may be identical or different and $R_h$ is as hereinbefore defined.

By the above-mentioned cycloalkyl groups, as defined, is meant both monocyclic and also polycyclic ring systems, while the polycyclic groups may be annelated, spiro-linked or bridged in structure, e.g., the polycyclic groups may be decalin, octahydroindene, norbornane, spiro[4,4]nonane, spiro[4,5]decane, bicyclo[2,1,1]hexane, bicyclo[2,2,2]octane, bicyclo[3,2,1]octane, bicyclo[3,2,2]nonane, bicyclo[3,3,1]nonane, bicyclo[3,3,2]decane, or adamantine.

Unless otherwise stated, the above-mentioned alkyl, alkenyl, and alkynyl groups may be straight-chain or branched.

The tautomers, enantiomers, diastereomers, the mixtures thereof, the prodrugs thereof, and the salts thereof.

The carboxy groups mentioned in the definition of the abovementioned groups may be replaced by a group which can be converted into a carboxy group in vivo or by a group which is negatively charged under physiological conditions, Furthermore, the amino and imino groups mentioned in the definition of the abovementioned groups may be substituted by a group which can be cleaved in vivo. Such groups are described for example in WO 98/46576 and by N. M. Nielsen et al. in International Journal of Pharmaceutics 39, 75–85 (1987).

By a group which can be converted in vivo into a carboxy group is meant, for example, a hydroxymethyl group, a carboxy group esterified with an alcohol, wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol, wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl, or $C_{2-6}$-alkanoyl group, and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol, or phenyl-$C_{3-5}$-alkynol, with the proviso that no bonds to the oxygen atom start from a carbon atom that carries a double or triple bond, a $C_{3-8}$-cycloalkyl-$C_{1-3}$-alkanol, a bicycloalkanol with a total of 8 to 10 carbon atoms that may additionally be substituted in the bicycloalkyl moiety by one or two $C_{1-3}$-alkyl groups, a 1,3-dihydro-3-oxo-1-isobenzofuranol, or an alcohol of formula

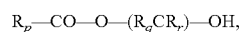

wherein $R_p$ denotes a $C_{1-8}$-alkyl, $C_{5-7}$-cycloalkyl, $C_{1-8}$-alkyloxy, $C_{5-7}$-cycloalkyloxy, phenyl, or phenyl-$C_{1-3}$-alkyl group, $R_q$ denotes a hydrogen atom, a $C_{1-3}$-alkyl, $C_{5-7}$-cycloalkyl, or phenyl group and $R_r$ denotes a hydrogen atom or a $C_{1-3}$-alkyl group, By a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl, or perfluoro-$C_{1-6}$-alkylsulphonylaminocarbonyl group.

By a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—($R_qCR_r$)—O—CO—, $C_{1-6}$-alkyl-CO—NH—($R_sCR_t$)—O—CO— or $C_{1-6}$-alkyl-CO—O—($R_sCR_t$)—($R_sCR_t$)—O—CO— group, wherein $R_p$ to $R_r$ are as hereinbefore defined, and $R_s$ and $R_t$, which may be identical or different, denote hydrogen atoms or $C_{1-3}$-alkyl groups.

Moreover, unless otherwise stated, the saturated alkyl and alkoxy moieties containing more than 2 carbon atoms mentioned in the definitions above also include the branched isomers thereof such as the isopropyl, tert.butyl, isobutyl group, etc.

$R^1$ may denote for example a 2-cyanobenzyl, 3-fluorobenzyl, 3-methoxybenzyl, 4-bromo-2-cyanobenzyl, 3-chloro-2-cyanobenzyl, 2-cyano-4-fluorobenzyl, 3,5-dimethoxybenzyl, 2,6-dicyanobenzyl, 5-cyanofuranylmethyl, oxazolylmethyl, isoxazolylmethyl, 5-methoxycarbonylthienylmethyl, pyridinylmethyl, 3-cyanopyridin-2-ylmethyl, 6-cyanopyridin-2-ylmethyl, 6-fluoropyridin-2-ylmethyl, 3-(2-cyanophenyl)-prop-2-enyl, 3-(pyridin-2-yl)-prop-2-enyl, 3-(pentafluorophenyl)-prop-2-enyl, phenylcarbonylmethyl, 3-methoxyphenylcarbonylmethyl, naphthyl-1-methyl, 4-cyanonaphth-1-ylmethyl, quinolin-1-ylmethyl, 4-cyano-quinolin-1-ylmethyl, isoquinolin-1-ylmethyl, 4-cyanoisoquinolin-1-ylmethyl, 4-cyanoisoquinolin-3-ylmethyl, 3-methyl-isoquinolin-1-ylmethyl, quinazolin-2-ylmethyl, 4-methylquinazolin-2-ylmethyl, [1,5]naphthiridin-2-ylmethyl, [1,5]naphthiridin-3-ylmethyl, quinoxalin-6-ylmethyl, or 2,3-dimethyl-quinoxalin-6-ylmethyl group.

$R^2$ may denote, for example, a hydrogen atom, a methyl, ethyl, propyl, 2-propyl, butyl, 2-butyl, 2-methylpropyl, tert.-butyl, cyclopropyl, cyclobutyl, cyclopentyl, cyclohexyl, 2-propen-1-yl, 2-propyn-1-yl, cyclopropylmethyl, phenyl, benzyl, 2-phenylethyl, 3-phenylpropyl, 2-hydroxyethyl, 2-methoxyethyl, 2-ethoxyethyl, 2-(dimethylamino)ethyl, pyrrolidin-1-yl, piperidin-1-yl, morpholin-1-yl, piperazin-1-yl, carboxy, methoxycarbonyl, ethoxycarbonyl, carboxymethyl, (methoxycarbonyl)methyl, aminocarbonyl, methylaminocarbonyl, dimethylaminocarbonyl, pyrrolidinocarbonyl, piperidinocarbonyl, morpholinocarbonyl, (aminocarbonyl)methyl, (methylaminocarbonyl)methyl, (dimethylaminocarbonyl)methyl, (pyrrolidinocarbonyl)methyl, (piperidinocarbonyl)methyl, (morpholinocarbonyl)methyl, cyanomethyl, 2-cyanoethyl, or pyridinyl group.

$R^3$ may denote for example a 2-propen-1-yl, 2-methyl-2-propen-1-yl, 1-buten-1-yl, 2-buten-1-yl, 3-buten-1-yl, 2-methyl-2-buten-1-yl, 3-methyl-2-buten-1-yl, 2,3-dimethyl-2-buten-1-yl, 3-methyl-3-buten-1-yl, 1-cyclopenten-1-ylmethyl, (2-methyl-1-cyclopenten-1-yl)methyl, 1-cyclohexen-1-ylmethyl, 2-propyn-1-yl, 2-butyn-1-yl, 3-butyn-1-yl, 2-chlorobenzyl, 2-bromobenzyl, 2-iodobenzyl, 2-cyanobenzyl, 3-fluorobenzyl, 2-methoxybenzyl, 2-furanylmethyl, 3-furanylmethyl, 2-thienylmethyl, or 3-thienylmethyl group.

$R^4$ may denote for example a (2-aminocyclopropyl)amino, N-(2-aminocyclopropyl)-N-methyl-amino, (2-aminocyclobutyl)amino, N-(2-aminocyclobutyl)-N-methyl-amino, N-(3-aminocyclobutyl)-N-methyl-amino, N-(2-aminoethyl)-N-methyl-amino, N-(1-aminoprop-2-yl)-N-methyl-amino, N-(2-aminopropyl)-N-methyl-amino, N-(1-amino-2-methyl-prop-2-yl)-N-methyl-amino, N-(2-amino-2-methyl-propyl)-N-methyl-amino, N-[(1-aminocyclopropyl)methyl]-N-methyl-amino, or N-(1-aminomethylcyclopropyl)-N-methyl-amino group.

Preferred compounds of general formula I are those wherein
$R^1$ and $R^4$ are as hereinbefore defined,
X denotes a nitrogen atom or a —CH group,
$R^2$ denotes a hydrogen atom, a $C_{1-4}$-alkyl, $C_{3-6}$-cycloalkyl or phenyl group and
$R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl, methoxybenzyl or cyanobenzyl group, the enantiomers, the diastereomers, the mixtures thereof and the salts thereof.

Particularly preferred compounds of general formula I are those wherein
$R^1$ denotes a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, naphthyridinylmethyl or benzotriazolylmethyl group which may be substituted in each case by one or two fluorine, chlorine, bromine atoms or one or two cyano, nitro, amino, $C_{1-3}$-alkyl, $C_{1-3}$-alkyloxy and morpholinyl groups, while the substituents are identical or different,
X denotes a nitrogen atom or a —CH group,
$R^2$ denotes a hydrogen atom,
$R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl or cyanobenzyl group and
$R^4$ denotes an N-(2-aminoethyl)-N-methyl-amino group wherein the ethyl group may be substituted by 1 to 4 methyl groups, the tautomers, the mixtures thereof and the salts thereof.

Most particularly preferred are those compounds of general formula I wherein
$R^1$ denotes a isoquinolinylmethyl, quinazolinylmethyl or benzyl group which may be substituted by a methyl or cyano group,
X denotes a nitrogen atom or a —CH group,
$R^2$ denotes a hydrogen atom,
$R^3$ denotes a 2-butyn-1-yl group and
$R^4$ denotes an N-(2-aminoethyl)-N-methyl-amino, N-(2-aminopropyl)-N-methyl-amino or N-(2-amino-2-methylpropyl)-N-methyl-amino group, the tautomers and the salts thereof.

The following preferred compounds may be mentioned by way of example:

(a) 2-[N-(2-aminoethyl)-N-methyl-amino]-3-(2-butyn-1-yl)-5-[(4-methyl-quinazolin-2-yl)methyl]-3,5-dihydro-imidazo[4,5-d]pyridazin-4-one
(b) 2-[N-(2-aminoethyl)-N-methyl-amino]-3-(2-butyn-1-yl)-5-[(3-methyl-isoquinolin-1-yl)methyl]-3,5-dihydro-imidazo[4,5-d]pyridazin-4-one
(c) (S)-2-[N-(2-aminopropyl)-N-methyl-amino]-3-(2-butyn-1-yl)-5-(2-cyanophenylmethyl)-3,5-dihydro-imidazo[4,5-d]pyridazin-4-one
(d) 2-[N-(2-amino-2-methylpropyl)-N-methyl-amino]-3-(2-butyn-1-yl)-5-(2-cyanophenylmethyl)-3,5-dihydro-imidazo[4,5-d]pyridazin-4-one
(e) (S)-2-[N-(2-aminopropyl)-N-methyl-amino]-3-(2-butyn-1-yl)-5-[(4-methyl-quinazolin-2-yl)methyl]-3,5-dihydro-imidazo[4,5-d]pyridazin-4-one
(f) 2-[N-(2-aminoethyl)-N-methyl-amino]-3-(2-butyn-1-yl)-5-[(3-methyl-isoquinolin-1-yl)methyl]-3,5-dihydro-imidazo[4,5-c]pyridin-4-one (g) (S)-2-[N-(2-aminopropyl)-N-methyl-amino]-3-(2-butyn-1-yl)-5-[(4-cyano-isoquinolin-3-yl)methyl]-3,5-dihydro-imidazo[4,5-c]pyridin-4-one and the tautomers and the salts thereof.

According to the invention the compounds of general formula I are obtained by methods known, per se, for example by the following methods:

A) Reacting a Compound of General Formula II

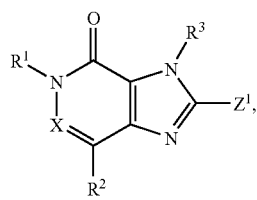

wherein

R¹ to R³ and X are as hereinbefore defined and

Z¹ denotes a leaving group such as a halogen atom, a substituted hydroxy, mercapto, sulphinyl, sulphonyl or sulphonyloxy group such as a chlorine or bromine atom, a methanesulphonyl or methanesulphonyloxy group, with R⁴—H or salts thereof, where R⁴ is as hereinbefore defined.

The reaction is expediently carried out in a solvent such as isopropanol, butanol, tetrahydrofuran, dioxane, dimethylformamide, dimethylsulphoxide, ethyleneglycolmonomethylether, ethyleneglycoldiethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may, however, also be carried out without a solvent in an excess of ethylenediamine derivative with conventional heating or in the microwave oven.

B) Deprotecting a Compound of General Formula III

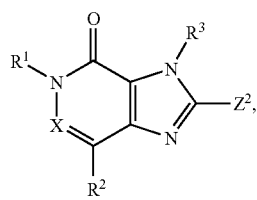

wherein

R¹, R², R³ and X are as hereinbefore defined and

Z² denotes one of the groups mentioned hereinbefore for R⁴ which contain an amino group not directly bound to the basic imidazopyridazinone structure which is Boc-protected in Z², where Boc denotes a tert.-butyloxycarbonyl group.

The tert.-butyloxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether at temperatures between 0 and 80° C.

In the reactions described hereinbefore, any reactive groups present such as amino, alkylamino or imino groups may be protected during the reaction by conventional protecting groups which are cleaved again after the reaction.

For example, protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g., in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g., in the presence of iodotrimethylsilane, at temperatures between 0° C. and 120° C., preferably at temperatures between 10° C. and 100° C.

However, a benzyl, methoxybenzyl or benzyloxycarbonyl group is cleaved, for example, hydrogenolytically, e.g., with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0° C. and 100° C., but preferably at ambient temperatures between 20° C. and 60° C., and at a hydrogen pressure of 1 to 7 bar, but preferably from 3 to 5 bar. However, a 2.4-dimethoxybenzyl group is preferably cleaved in trifluoroacetic acid in the presence of anisole.

A tert.-butyl or tert. butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50° C. and 120° C. or by treating with sodium hydroxide solution, optionally in the presence of a solvent such as tetrahydrofuran, at temperatures between 0° C. and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20° C. and 50° C.

Moreover, the compounds of general formula I obtained may be resolved into their enantiomers and/or diastereomers, as mentioned hereinbefore. Thus, for example, cis/trans mixtures may be resolved into their cis- and trans-isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known, per se (cf. Allinger N. L. and Eliel E. L. in "Topics in Stereochemistry", Vol. 6, Wiley Interscience, 1971), into their optical enantiomers and compounds of general formula I with at least 2 asymmetric carbon atoms may be resolved into their diastereomers on the basis of their physical-chemical differences using methods known, per se, e.g., by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as, e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+)- or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of formula (I), if they contain a carboxy group, may if desired be converted into the salts thereof with inorganic or organic bases, particularly for pharmaceutical use into the physiologically acceptable salts thereof. Suitable bases for this include, for example, sodium hydroxide, potassium hydroxide, cyclohexylamine, ethanolamine, diethanolamine and triethanolamine.

The compounds of general formulae II and III used as starting compounds are either known from the literature or may be prepared by methods known from the literature (see Examples I to XI).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757–5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl, pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potencies of the test substances in question, expressed as $IC_{50}$ values, were calculated from dosage/activity curves consisting of 11 measured points in each case. The following results were obtained:

| Compound (Example No.) | DPP IV inhibition $IC_{50}$ [nM] |
|---|---|
| 1 | 1 |
| 1(1) | 10 |
| 1(2) | 34 |
| 2 | 76 |
| 2(1) | 336 |
| 3 | 2 |

The compounds prepared according to the invention are well tolerated as no toxic side effects could be detected in rats after the oral administration of 10 mg/kg of the compound of Example 1, for example.

In view of their ability to inhibit DPP-IV activity, the compounds of general formula I according to the invention, and the corresponding pharmaceutically acceptable salts thereof, are suitable for influencing any conditions or diseases that can be affected by the inhibition of the DPP-IV activity. It is therefore to be expected that the compounds according to the invention will be suitable for the prevention or treatment of diseases or conditions such as type I and type II diabetes mellitus, diabetic complications (e.g., retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as, e.g., apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example.

Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as metformin, sulphonylureas (e.g., glibenclamide, tolbutamide, glimepiride), nateglinide, repaglinide, thiazolidinediones (e.g., rosiglitazone, pioglitazone), PPAR-gamma agonists (e.g., GI 262570) and antagonists, PPAR-gamma/alpha modulators (e.g., KRP 297), alpha-glucosidase inhibitors (e.g., acarbose, voglibose), other DPPIV inhibitors, alpha2 antagonists, insulin and insulin analogues, GLP-1 and GLP-1 analogues (e.g., exendin-4) or amylin. Also, combinations with SGLT2 inhibitors such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g., simvastatin, atorvastatin), fibrates (e.g., bezafibrate, fenofibrate), nicotinic acid and its derivatives, PPAR-alpha agonists, PPAR-delta agonists, ACAT inhibitors (e.g., avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or active substances for the treatment of obesity, such as, e.g., sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $\beta_3$-agonists such as SB-418790 or AD-9677 as well as agonists of the 5HT2c receptor.

It is also possible to combine the compounds with drugs for treating high blood pressure such as, e.g., AII antagonists or ACE inhibitors, diuretics, $\beta$-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions, or suppositories.

The Examples that follow are intended to illustrate the invention:

Preparation of the Starting Compounds:

EXAMPLE I

Dimethyl 2-bromo-1-(2-butyn-1-yl)-1H-imidazole-4,5-dicarboxylate

A solution of 15.0 g dimethyl 2-bromo-imidazole-4,5-dicarboxylate, 5.15 ml 1-bromo-2-butyne and 50 ml N,N-diisopropylethylamine in 280 ml of tetrahydrofuran is refluxed for one hour. The mixture is concentrated by evaporation, the residue is combined with approx. 100 ml of water and extracted three times with 70 ml of ethyl acetate. The extracts are washed with 50 ml of water, dried and evaporated down. The crude product thus obtained is purified by column chromatography through silica gel with methylene chloride/ethanol (1:0->49:1) as eluant.

Yield: 13.50 g (75% of theory)

$R_f$ value: 0.82 (silica gel, methylene chloride/ethanol=9:1)

Mass spectrum (ESI$^+$): m/z=315/317 (Br) [M+H]$^+$

EXAMPLE II

Methyl 2-bromo-3-(2-butyn-1-yl)-5-formyl-3H-imidazol-4-carboxylate 43 ml of a 1 M solution of diisobutylaluminium hydride in tetrahydrofuran are added dropwise within 20 minutes to a solution of 13.5 g of dimethyl 2-bromo-1-(2-butyn-1-yl)-1H-imidazole-4,5-dicarboxylate in 220 ml of tetrahydrofuran under an argon atmosphere at −70° C. The mixture is stirred for a further four hours at −70° C., then 20 ml of a mixture of 1 M hydrochloric acid and tetrahydrofuran are added dropwise. After heating to ambient temperature approx. 200 ml of water are added and the mixture is extracted three times with 70 ml of ethyl acetate. The combined extracts are dried and evaporated down. The crude product thus obtained is purified by column chromatography through silica gel with petroleum ether/ethyl acetate (4:1->1:1) as eluant.

Yield: 6.40 g (52% of theory)

Mass spectrum (ESI$^+$): m/z=285/287 (Br) [M+H]$^+$

EXAMPLE III 2-bromo-3-(2-butyn-1-yl)-3,5-dihydro-imidazo[4,5-d]pyridazin-4-one 0.31 ml hydrazine hydrate, dissolved in 1 ml of ethanol, are added dropwise at ambient temperature to a solution of 1.80 g methyl 2-bromo-3-(2-butyn-1-yl)-5-formyl-3H-imidazole-4-carboxylate in 25 ml of ethanol. Five minutes later 1.5 ml concentrated acetic acid are added, and the mixture is refluxed for 30 minutes. After cooling the solid precipitate is suction filtered, washed with 10 ml of ethanol and 20 ml diethyl ether and dried.

Yield: 1.25 g (74% of theory)

Mass spectrum (ESI$^+$): m/z=267/269 (Br) [M+H]$^+$

EXAMPLE IV 2-bromo-3-(2-butyn-1-yl)-5-[(4-methyl-quinazolin-2-yl)methyl]-3,5-dihydro-imidazo[4,5-d]pyridazin-4-one A mixture of 365 mg 2-bromo-3-(2-butyn-1-yl)-3,5-dihydro-imidazo[4,5-d]pyridazin-4-one, 265 mg 2-chloromethyl-4-methyl-quinazoline and 210 mg potassium carbonate in 6 ml acetonitrile is stirred for 17 h at ambient temperature. Then the reaction mixture is filtered through 5 g aluminium oxide with ethyl acetate and the filtrate is evaporated down. The residue is triturated in diisopropylether, separated from the ether and dried.

Yield: 300 mg (53% of theory)

Mass spectrum (ESI$^+$): m/z=423/425 (Br) [M+H]$^+$

The following compounds are obtained analogously to Example IV:

(1) 2-bromo-3-(2-butyn-1-yl)-5-[(3-methyl-isoquinolin-1-yl)methyl]-3,5-dihydro-imidazo[4,5-d]pyridazin-4-one Mass spectrum (ESI$^+$): m/z=422/424 (Br) [M+H]$^+$ (2) 2-bromo-3-(2-butyn-1-yl)-5-(2-cyanophenylmethyl)-3,5-dihydro-imidazo[4,5-d]pyridazin-4-one Mass spectrum (ESI$^+$): m/z=382/384 (Br) [M+H]$^+$ (3) 2-bromo-3-(2-butyn-1-yl)-5-(4-cyano-isoquinolin-3-ylmethyl)-3,5-dihydro-imidazo[4,5-d]pyridazin-4-one Mass spectrum (ESI$^+$): m/z=463/465 (Br) [M+H]$^+$

EXAMPLE V (S)-2-[(2-aminopropyl)amino]-3-(2-butyn-1-yl)-5-(2-cyanophenylmethyl)-3,5-dihydro-imidazo[4,5-d]pyridazin-4-one A mixture of 0.36 g 2-bromo-3-(2-butyn-1-yl)-5-(2-cyanophenylmethyl)-3,5-dihydro-imidazo[4,5-d]pyridazin-4-one, 0.42 g (S)-1,2-diaminopropane dihydrochloride and 0.52 g potassium carbonate in 6 ml N-methylpyrrolidone is stirred for 2.5 h at 120° C. Then saturated aqueous sodium chloride solution is added and the precipitate formed is separated off. The aqueous phase is extracted with ethyl acetate, the combined organic phases are dried over sodium sulphate and evaporated down.

Yield: 580 mg (approx. 60% pure)

$R_f$ value: 0.30 (silica gel, methylene chloride/methanol/ammonium hydroxide=90:10:0.1)

The following compound is obtained analogously to Example V:

(1) 2-[(2-amino-2-methyl-propyl)amino]-3-(2-butyn-1-yl)-5-(2-cyanophenylmethyl)-3,5-dihydro-imidazo[4,5-d]pyridazin-4-one $R_f$ value: 0.25 (silica gel, methylene chloride/methanol/ammonium hydroxide=90:10:0.1)

(2) (S)-2-[(2-benzyloxycarbonylamino-prop-1-yl)amino]-3-(2-butyn-1-yl)-5-[(4-methyl-quinazolin-2-yl)methyl]-3,5-dihydro-imidazo[4,5-d]pyridazin-4-one Product (2) was obtained by reacting 2-bromo-3-(2-butyn-1-yl)-5-[(4-methyl-quinazolin-2-yl)methyl]-3,5-dihydro-imidazo[4,5-d]pyridazin-4-one with (S)—N-(2-benzyloxycarbonylamino-prop-1-yl)-N-methyl-amine.

Mass spectrum (ESI$^+$): m/z=565 [M+H]$^+$ (3) (S)-2-[(2-aminopropyl)amino]-3-(2-butyn-1-yl)-5-(4-cyano-isoquinolin-3-ylmethyl)-3,5-dihydro-imidazo[4,5-d]pyridazin-4-one $R_f$ value: 0.30 (silica gel, methylene chloride/methanol/ammonium hydroxide=90:10:0.1)

EXAMPLE VI (S)-2-[(2-tert-butyloxycarbonylamino-propyl)amino]-3-(2-butyn-1-yl)-5-(2-cyanophenylmethyl)-3,5-dihydro-imidazo[4,5-d]pyridazin-4-one 0.73 g di-tert. butyl pyrocarbonate are added at ambient temperature to a solution of 1.04 g (S)-2-[(2-aminopropyl)amino]-3-(2-butyn-1-yl)-5-(2-cyanophenylmethyl)-3,5-dihydro-imidazo[4,5-d]pyridazin-4-one and 0.54 ml triethylamine in 200 ml dichloromethane. The solution is stirred for 16 h at ambient temperature and then evaporated down. The residue is taken up in ethyl acetate and in each case washed once with water, dilute citric acid, water and saturated aqueous sodium chloride solution. Then the organic phase is dried over sodium sulphate and evaporated down. The residue is purified by chromatography through silica gel (petroleum ether/ethyl acetate 1:1).

Yield: 0.40 g (30% of theory)

Mass spectrum (ESI$^+$): m/z=476 [M+H]$^+$

The following compound is obtained analogously to Example VI:

(1) 2-[(2-tert-butyloxycarbonylamino-2-methyl-propyl)amino]-3-(2-butyn-1-yl)-5-(2-cyanophenylmethyl)-3,5-dihydro-imidazo[4,5-d]pyridazin-4-one Mass spectrum (ESI$^+$): m/z=490 [M+H]$^+$ (2) (S)-2-[(2-tert-butyloxycarbonylamino-propyl)amino]-3-(2-butyn-1-yl)-5-(4-cyanoisoquinolin-3-ylmethyl)-3,5-dihydro-imidazo[4,5-d]pyridazin-4-one Mass spectrum (ESI$^+$): m/z=557 [M+H]$^+$

EXAMPLE VII (S)-2-[N-(2-tert-butyloxycarbonylamino-propyl)-N-methyl-amino]-3-(2-butyn-1-yl)-5-(2-cyanophenylmethyl)-3,5-dihydro-imidazo[4,5-d]pyridazin-4-one 0.96 g potassium-tert-butoxide are added to an ice-cooled solution of 0.39 g (S)-2-[(2-tert-butyloxycarbonylamino-propyl)amino]-3-(2-butyn-1-yl)-5-(2-cyanophenylmethyl)-3,5-dihydro-imidazo[4,5-d]pyridazin-4-one in 5 ml dimethylsulphoxide. The mixture is stirred at ambient temperature, until the solution is clear. Then 53 µl methyl iodide are added, and the solution is stirred for a further 3.5 h at ambient temperature. Then water is added to the reaction solution, the precipitate formed is separated off and washed with water. The dried precipitate is purified by chromatography through silica gel (petroleum ether/ethyl acetate 1:1).

Yield: 0.26 g (66% of theory)
Mass spectrum (ESI$^+$): m/z=490 [M+H]$^+$

The following compound is obtained analogously to Example VII:
(1) 2-[N-(2-tert-butyloxycarbonylamino-2-methyl-propyl)-N-methyl-amino]-3-(2-butyn-1-yl)-5-(2-cyanophenylmethyl)-3,5-dihydro-imidazo[4,5-d]pyridazin-4-one
Mass spectrum (ESI$^+$): m/z=504 [M+H]$^+$
(2) (S)-2-[N-(2-tert-butyloxycarbonylamino-propyl)-N-methyl-amino]-3-(2-butyn-1-yl)-5-(4-cyano-isoquinolin-3-ylmethyl)-3,5-dihydro-imidazo[4,5-d]pyridazin-4-one
Mass spectrum (ESI$^+$): m/z=571 [M+H]$^+$

EXAMPLE VIII

Methyl 2-bromo-5-(trans-2-methoxy-vinyl)-3H-imidazole-4-carboxylate

Under an argon atmosphere 38 ml of a 0.5 M solution of potassium-bis(trimethylsilyl)amide in toluene are added dropwise to an ice-cooled solution of 6.64 g methoxymethyltriphenyl phosphonium chloride in 140 ml of tetrahydrofuran over 10 min. The reaction mixture is stirred for a further 15 min in the ice bath and then cooled to −70° C. Then a solution of 4.41 g methyl 2-bromo-3-(2-butyn-1-yl)-5-formyl-3H-imidazole-4-carboxylate in 40 ml of tetrahydrofuran is added dropwise over 30 min. After a further 45 min stirring at −70° C. the solution is heated to ambient temperature and stirred for another 1 h at this temperature. Then water is added to the reaction solution and this is extracted with ethyl acetate. The organic extracts are dried over sodium sulphate, the solvent is removed and the residue is chromatographed through silica gel (cyclohexane/ethyl acetate 9:1->7:3).

Yield: 2.67 g (55% of theory), pure trans compound
Mass spectrum (ESI$^+$): m/z=313/315 (Br) [M+H]$^+$

EXAMPLE IX 2-bromo-5-(trans-2-methoxy-vinyl)-3H-imidazole-4-carboxylic acid

A solution of 2.20 g lithium hydroxide in 175 ml of water is added to a solution of 3.50 g methyl 2-bromo-5-(trans-2-methoxy-vinyl)-3H-imidazole-4-carboxylate in 140 ml of tetrahydrofuran. The solution is stirred for 4 h at ambient temperature. Then 92 ml aqueous 1 M hydrochloric acid are added, and the solution is cooled in the ice bath. The precipitate is separated off, washed with water and dried.

Yield: 3.30 g (99% of theory)
Mass spectrum (ESI$^+$): m/z=299/301 (Br) [M+H]$^+$

EXAMPLE X 2-bromo-3-(2-butyn-1-yl)-5-(trans-2-methoxy-vinyl)-3H-imidazole-4-carboxylic acid-(3-methyl-isoquinolin-1-ylmethyl)-amide A solution of 3.50 g 2-bromo-5-(trans-2-methoxy-vinyl)-3H-imidazole-4-carboxylic acid and 1.30 g TBTU in 1.20 ml triethylamine and 30 ml of dimethylformamide is stirred for 15 min at ambient temperature. Then 1.09 g 3-methyl-isoquinolin-1-yl-methylamine are added, and the resulting suspension is stirred for 4 h at ambient temperature. Then ice-cooled water is added and the precipitate is separated off. The precipitate is dissolved in dichloromethane, the solution is dried over sodium sulphate and the solvent is removed.

Yield: 1.38 g (78% of theory)
Mass spectrum (ESI$^+$): m/z=453/455 (Br) [M+H]$^+$

EXAMPLE XI 2-bromo-3-(2-butyn-1-yl)-5-[(3-methyl-isoquinolin-1-yl)methyl]-3,5-dihydro-imidazo [4,5-c]pyridin-4-one in a 1:1-mixture with 2-chloro-3-(2-butyn-1-yl)-5-[(3-methyl-isoquinolin-1-yl)methyl]-3,5-dihydro-imidazo[4,5-c]pyridin-4-one 0.74 g 2-bromo-3-(2-butyn-1-yl)-5-(trans-2-methoxy-vinyl)-3H-imidazole-4-carboxylic acid-(3-methyl-isoquinolin-1-ylmethyl)-amide are stirred in 35 ml aqueous 4 M hydrochloric acid for 3 h at 85° C. After cooling to ambient temperature dichloromethane is added and the solution is made alkaline with sodium hydroxide solution. The organic phase is separated off and the aqueous phase is extracted twice with dichloromethane. The combined organic phases are dried over sodium sulphate, the solvent is removed and the residue is purified through silica gel (dichloromethane/methanol 99:1->95:5).

Yield: 0.39 g (1:1 mixture of the two title compounds)
Mass spectrum (ESI$^+$): m/z=421/423 (Br) [M+H]+and m/z=377/379 (Cl) [M+H]$^+$ Preparation of the End Compounds:

EXAMPLE 1

2-[N-(2-aminoethyl)-N-methyl-amino]-3-(2-butyn-1-yl)-5-[(4-methyl-quinazolin-2-yl) methyl]-3,5-dihydro-imidazo[4,5-d]pyridazin-4-one

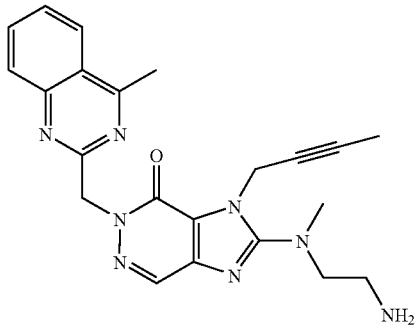

A mixture of 300 mg 2-bromo-3-(2-butyn-1-yl)-5-[(4-methyl-quinazolin-2-yl)methyl]-3,5-dihydro-imidazo[4,5-d]pyridazin-4-one, 400 mg N-methyl-ethylenediamine and 210 mg potassium carbonate in 6 ml dimethylsulphoxide is stirred for 8 h at 60° C. Then saturated aqueous sodium chloride solution is added and the aqueous phase is extracted with ethyl acetate. The combined organic phases are dried over sodium sulphate and evaporated down. The crude product is purified by chromatography through a silica gel column with methylene chloride/methanol. (3:2) as eluant.

Yield: 85 mg (29% of theory)

Mass spectrum (ESI$^+$): m/z=417 [M+H]$^+$

The following compound is obtained analogously to Example 1:

(1) 2-[N-(2-aminoethyl)-N-methyl-amino]-3-(2-butyn-1-yl)-5-[(3-methyl-isoquinolin-1-yl)methyl]-3,5-dihydro-imidazo[4,5-d]pyridazin-4-one

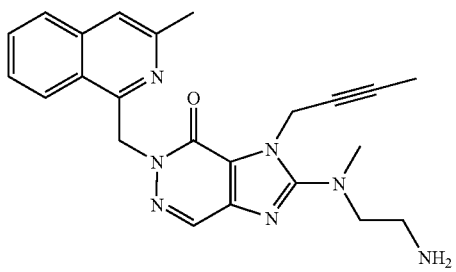

Mass spectrum (ESI$^+$): m/z=416 [M+H]$^+$ (2) 2-[N-(2-aminoethyl)-N-methyl-amino]-3-(2-butyn-1-yl)-5-[(3-methyl-isoquinolin-1-yl)methyl]-3,5-dihydro-imidazo[4,5-c]pyridin-4-one

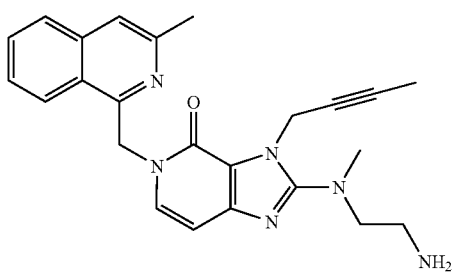

Product (2) was obtained by reacting a 1:1 mixture of 2-bromo-3-(2-butyn-1-yl)-5-[(3-methyl-isoquinolin-1-yl)methyl]-3,5-dihydro-imidazo[4,5-c]pyridin-4-one and 2-chloro-3-(2-butyn-1-yl)-5-[(3-methyl-isoquinolin-1-yl)methyl]-3,5-dihydro-imidazo[4,5-c]pyridin-4-one with N-methyl-ethylenediamine according to the instructions described above.

Mass spectrum (ESI$^+$): m/z=415 [M+H]$^+$

EXAMPLE 2

(S)-2-[N-(2-amino-propyl)-N-methyl-amino]-3-(2-butyn-1-yl)-5-(2-cyanophenylmethyl)-3,5-dihydro-imidazo[4,5-d]pyridazin4-one

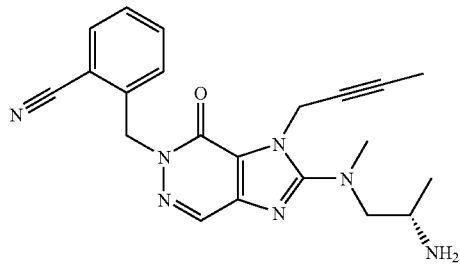

1.4 ml trifluoroacetic acid are added dropwise to a solution of 250 mg (S)-2-[N-(2-tert-butyloxycarbonylamino-propyl)-N-methyl-amino]-3-(2-butyn-1-yl)-5-(2-cyanophenylmethyl)-3,5-dihydro-imidazo[4,5-d]pyridazin-4-one in 5 ml dichloromethane. The solution is stirred for 4 h at ambient temperature, then diluted with dichloromethane and made alkaline with saturated aqueous sodium carbonate solution. The organic phase is separated off, washed with water, dried over magnesium sulphate and evaporated down. The residue is stirred with tert-butylmethylether and after separation of the ether dried in vacuo at 40-50° C.

Yield: 161 mg (81% of theory)

Mass spectrum (ESI$^+$): m/z=390 [M+H]$^+$

The following compound is obtained analogously to Example 2:

(1) 2-[N-(2-amino-2-methyl-propyl)-N-methyl-amino]-3-(2-butyn-1-yl)-5-(2-cyanophenylmethyl)-3,5-dihydro-imidazo[4,5-d]pyridazin-4-one

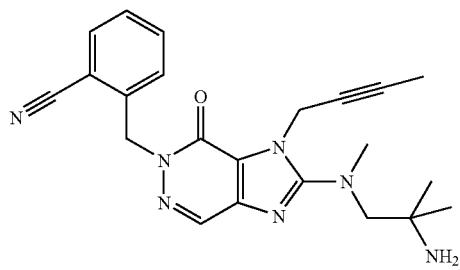

Mass spectrum (ESI$^+$): m/z=404 [M+H]$^+$ (2) (S)-2-[N-(2-amino-propyl)-N-methyl-amino]-3-(2-butyn-1-yl)-5-(4-cyano-isoquinolin-3-ylmethyl)-3,5-dihydro-imidazo[4,5-d]pyridazin-4-one

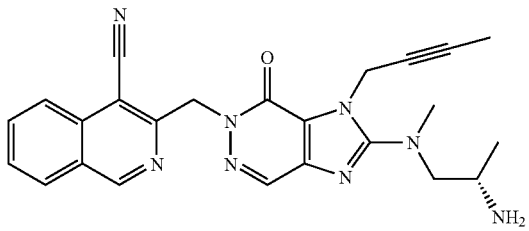

Mass spectrum (ESI⁺): m/z=441 [M+H]⁺

EXAMPLE 3

(S)-2-[N-(2-aminopropyl)-N-methyl-amino]-3-(2-butyn-1-yl)-5-[(4-methyl-quinazolin-2-yl)methyl]-3,5-dihydro-imidazo[4,5-d]pyridazin-4-one

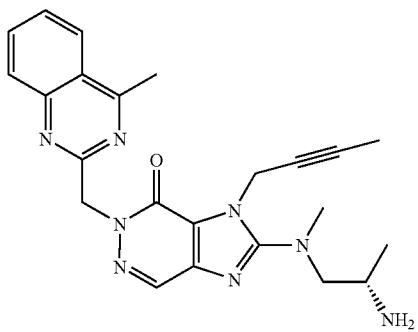

40 μl iodotrimethylsilane are added to a solution of 130 mg (S)-2-[(2-benzyloxycarbonylamino-prop-1-yl)amino]-3-(2-butyn-1-yl)-5-[(4-methyl-quinazolin-2-yl)methyl]-3,5-dihydro-imidazo[4,5-d]pyridazin-4-one in 3 ml dichloromethane. After stirring at ambient temperature for 1 and 3 h, a further 100 μl of iodotrimethylsilane are added on each occasion. The solution is stirred for a further 4 h at ambient temperature and then combined with 5 ml of methanol and evaporated down. Then 1 M hydrochloric acid is added and the aqueous phase is washed twice with dichloromethane. The aqueous phase is made alkaline with sodium carbonate and extracted three times with dichloromethane. The organic extracts are dried over sodium sulphate, the solvent is removed and the residue is purified through silica gel (dichloromethane/methanol 1:0–>3:1).

Yield: 30 mg (30% of theory)

Mass spectrum (ESI⁺): m/z=431 [M+H]⁺

The following compounds may also be obtained analogously to the foregoing Examples and other methods known from the literature:

(1) 2-[N-(2-aminoethyl)-N-methyl-amino]-3-(2-butyn-1-yl)-5-[(4-cyano-naphth-1-yl)methyl]-3,5-dihydro-imidazo[4,5-d]pyridazin-4-one (2) 2-[N-(2-aminoethyl)-N-methyl-amino]-3-(2-butyn-1-yl)-5-(2-cyano-phenylmethyl)-3,5-dihydro-imidazo[4,5-d]pyridazin-4-one (3) 2-[N-(2-amino-prop-1-yl)-N-methyl-amino]-3-(2-butyn-1-yl)-5-(quinoxalin-6-ylmethyl)-3,5-dihydro-imidazo[4,5-d]pyridazin-4-one (4) 2-[N-(2-aminocyclopropyl)amino]-3-(2-butyn-1-yl)-5-(2-cyano-phenylmethyl)-3,5-dihydro-imidazo[4,5-d]pyridazin-4-one (5) 2-[N-(2-amino-prop-1-yl)-N-methyl-amino]-3-(2-butyn-1-yl)-5-[(4-cyano-naphth-1-yl)methyl]-3,5-dihydro-imidazo[4,5-d]pyridazin-4-one (6) 2-[N-(2-amino-2-methyl-prop-1-yl)-N-methyl-amino]-3-(2-butyn-1-yl)-5-[(4-methyl-quinazolin-2-yl)methyl]-3,5-dihydro-imidazo[4,5-d]pyridazin-4-one (7) 2-[N-(2-amino-2-methyl-prop-1-yl)-N-methyl-amino]-3-(2-butyn-1-yl)-5-(phenylcarbonylmethyl)-3,5-dihydro-imidazo[4,5-d]pyridazin-4-one (8) 2-[N-(2-amino-prop-1-yl)-N-methyl-amino]-3-(2-butyn-1-yl)-5-[3-(2-nitrophenyl)prop-2-en-1-yl]-3,5-dihydro-imidazo[4,5-d]pyridazin-4-one (9) 2-[N-(1-aminocycloprop-1-ylmethyl)-N-methyl-amino]-3-(2-butyn-1-yl)-5-[(4-methyl-quinazolin-2-yl)methyl]-3,5-dihydro-imidazo[4,5-d]pyridazin-4-one

(10) 2-[N-(2-aminoethyl)-N-methyl-amino]-3-(2-butyn-1-yl)-5-[(3-chloro-2-cyanophenyl)methyl]-3,5-dihydro-imidazo[4,5-d]pyridazin-4-one

(11) 2-[N-(2-aminoethyl)-N-methyl-amino]-3-(2-butyn-1-yl)-5-([1,5]naphthyridin-2-ylmethyl)-3,5-dihydro-imidazo[4,5-d]pyridazin-4-one

(12) 2-[N-(2-aminoprop-1-yl)-N-methyl-amino]-3-(2-butyn-1-yl)-5-(quinoxalin-6-ylmethyl)-3,5-dihydro-imidazo[4,5-d]pyridazin-4-one

(13) 2-[N-(2-aminoethyl)-N-methyl-amino]-3-(2-butyn-1-yl)-5-(quinazolin-7-ylmethyl)-3,5-dihydro-imidazo[4,5-d]pyridazin-4-one

(14) 2-[N-(2-aminoprop-1-yl)-N-methyl-amino]-3-(2-butyn-1-yl)-5-[(1-cyano-isoquinolin-3-yl)methyl]-3,5-dihydro-imidazo[4,5-d]pyridazin-4-one

(15) 2-[N-(2-aminoethyl)-N-methyl-amino]-3-(2-butyn-1-yl)-5-[(4-morpholin-4-ylquinazolin-2-yl)methyl]-3,5-dihydro-imidazo[4,5-d]pyridazin-4-one

(16) 2-[N-(2-aminoprop-1-yl)-N-methyl-amino]-3-(2-butyn-1-yl)-5-[(4-phenyl-pyrimidin-2-yl)methyl]-3,5-dihydro-imidazo[4,5-d]pyridazin-4-one

(17) 2-[N-(2-aminoethyl)-N-methyl-amino]-3-(2-butyn-1-yl)-5-(2,3-dimethyl-quinoxalin-6-ylmethyl)-3,5-dihydro-imidazo[4,5-d]pyridazin-4-one

(18) 2-[N-(2-aminoethyl)-N-methyl-amino]-3-(2-butyn-1-yl)-5-[(1-cyano-isoquinolin-3-yl)methyl]-3,5-dihydro-imidazo[4,5-d]pyridazin-4-one

(19) 2-[N-(2-aminoethyl)-N-methyl-amino]-3-(2-butyn-1-yl)-5-[(3-methoxy-phenyl)carbonylmethyl]-3,5-dihydro-imidazo[4,5-d]pyridazin-4-one

(20) 2-[N-(2-aminoprop-1-yl)-N-methyl-amino]-3-(2-butyn-1-yl)-5-[(2-methoxy-phenyl)carbonylmethyl]-3,5-dihydro-imidazo[4,5-d]pyridazin-4-one

(21) 2-[N-(2-aminoethyl)-N-methyl-amino]-3-(2-buten-1-yl)-5-[(3-methyl-isoquinolin-1-yl)methyl]-3,5-dihydro-imidazo[4,5-d]pyridazin-4-one

(22) 2-[N-(2-amino-prop-1-yl)-N-methyl-amino]-3-(3-methyl-but-2-en-1-yl)-5-[(3-methyl-isoquinolin-1-yl)methyl]-3,5-dihydro-imidazo[4,5-d]pyridazin-4-one

(23) 2-[N-(2-aminoethyl)-N-methyl-amino]-3-(1-cyclopenten-1-yl)-5-[(3-methyl-isoquinolin-1-yl)methyl]-3,5-dihydro-imidazo[4,5-d]pyridazin-4-one

(24) 2-[N-(2-amino-2-methyl-prop-1-yl)-N-methyl-amino]-3-(1-buten-1-yl)-5-[(3-methyl-isoquinolin-1-yl)methyl]-3,5-dihydro-imidazo[4,5-d]pyridazin-4-one

(25) 2-[N-(2-aminoethyl)-N-methyl-amino]-3-[(2-chlorophenyl)methyl]-5-[(4-methyl-quinazolin-2-yl)methyl]-3,5-dihydro-imidazo[4,5-d]pyridazin-4-one

(26) 2-[N-(2-aminoethyl)-N-methyl-amino]-3-[(2-bromophenyl)methyl]-5-[(4-methyl-quinazolin-2-yl)methyl]-3,5-dihydro-imidazo[4,5-d]pyridazin-4-one

(27) 2-[N-(2-amino-2-methyl-prop-1-yl)-N-methyl-amino]-3-[(2-iodo-phenyl)methyl]-5-[(4-methyl-quinazolin-2-yl)methyl]-3,5-dihydro-imidazo[4,5-d]pyridazin-4-one

(28) 2-[N-(2-amino-prop-1-yl)-N-methyl-amino]-3-[(2-cyano-phenyl)methyl]-5-[(4-methyl-quinazolin-2-yl)methyl]-3,5-dihydro-imidazo[4,5-d]pyridazin-4-one

(29) 2-[N-(2-amino-prop-1-yl)-N-methyl-amino]-3-(furan-2-ylmethyl)-5-[(4-methyl-quinazolin-2-yl)methyl]-3,5-dihydro-imidazo[4,5-d]pyridazin-4-one

(30) 2-[N-(2-aminoethyl)-N-methyl-amino]-3-(thien-3-ylmethyl)-5-[(4-methyl-quinazolin-2-yl)methyl]-3,5-dihydro-imidazo[4,5-d]pyridazin-4-one

(31) 2-[N-(2-amino-prop-1-yl)-N-methyl-amino]-3-(2-butyn-1-yl)-5-[(4-methoxy-naphth-1-yl)methyl]-3,5-dihydro-imidazo[4,5-d]pyridazin-4-one

(32) 2-[N-(2-amino-prop-1-yl)-N-methyl-amino]-3-(2-butyn-1-yl)-5-[3-(pentafluorophenyl)prop-2-en-1-yl]-3,5-dihydro-imidazo[4,5-d]pyridazin-4-one

(33) 2-[(azetidin-3-yl)amino]-3-(2-butyn-1-yl)-5-[(4-methyl-quinazolin-2-yl)methyl]-3,5-dihydro-imidazo[4,5-d]pyridazin-4-one

(34) 2-[N-(azetidin-3-yl)-N-methyl-amino]-3-(2-butyn-1-yl)-5-[(4-methyl-quinazolin-2-yl)methyl]-3,5-dihydro-imidazo[4,5-d]pyridazin-4-one

(35) 2-[N-(2-amino-1,1,2-trimethylprop-1-yl)-N-methyl-amino]-3-(2-butyn-1-yl)-5-[(3-methyl-isoquinolin-1-yl)methyl]-3,5-dihydro-imidazo[4,5-d]pyridazin-4-one

(36) 2-[(3-methyl-azetidin-3-yl)amino]-3-(2-butyn-1-yl)-5-[(4-methyl-quinazolin-2-yl)-methyl]-3,5-dihydro-imidazo[4,5-d]pyridazin-4-one

(37) 2-[N-(2-amino-prop-1-yl)-N-methyl-amino]-3-(2-butyn-1-yl)-5-[(3-methyl-isoquinolin-1-yl)methyl]-3,5-dihydro-imidazo[4,5-d]pyridazin-4-one

(38) 2-[N-(2-amino-1-methyl-prop-1-yl)-N-methyl-amino]-3-(2-butyn-1-yl)-5-[(3-methyl-isoquinolin-1-yl)methyl]-3,5-dihydro-imidazo[4,5-d]pyridazin-4-one

(39) 2-[N-(2-amino-prop-1-yl)-N-methyl-amino]-3-(2-butyn-1-yl)-5-[(3-cyano-pyridin-2-yl)methyl]-3,5-dihydro-imidazo[4,5-d]pyridazin-4-one

(40) 2-[N-(2-amino-prop-1-yl)-N-methyl-amino]-3-(2-butyn-1-yl)-5-[(3-cyano-pyridin-2-yl)methyl]-3,5-dihydro-imidazo[4,5-c]pyridin-4-one

(41) 2-[N-(2-aminoethyl)-N-methyl-amino]-3-(2-butyn-1-yl)-5-[(4-methyl-quinazolin-2-yl)methyl]-3,5-dihydro-imidazo[4,5-c]pyridin-4-one

(42) 2-[N-(2-amino-prop-1-yl)-N-methyl-amino]-3-(2-butyn-1-yl)-5-[(4-methyl-quinazolin-2-yl)methyl]-3,5-dihydro-imidazo[4,5-c]pyridin-4-one

(43) 2-[N-(2-amino-prop-1-yl)-N-methyl-amino]-3-(2-butyn-1-yl)-5-([1,5]naphthyridin-2-ylmethyl)-3,5-dihydro-imidazo[4,5-d]pyridazin-4-one

(44) 2-[N-(2-amino-prop-1-yl)-N-methyl-amino]-3-(2-butyn-1-yl)-5-(4,6-dimethyl-pyrimidin-2-ylmethyl)-3,5-dihydro-imidazo[4,5-d]pyridazin-4-one

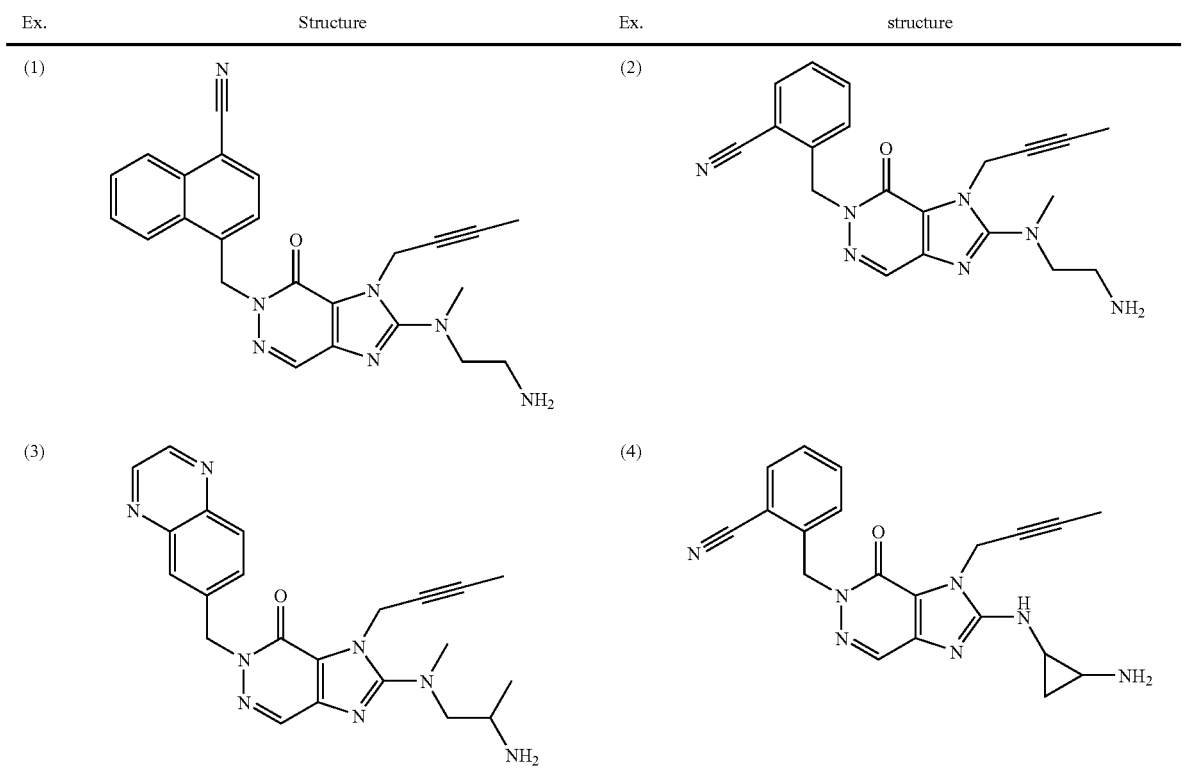

-continued

| Ex. | Structure | Ex. | structure |
|---|---|---|---|
| (5) | 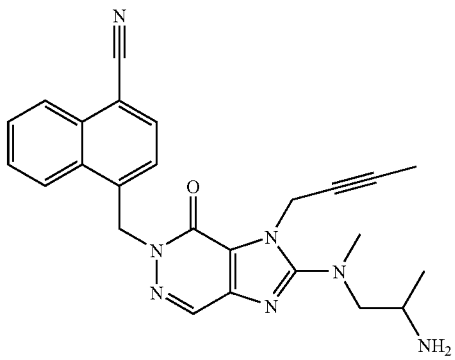 | (6) | 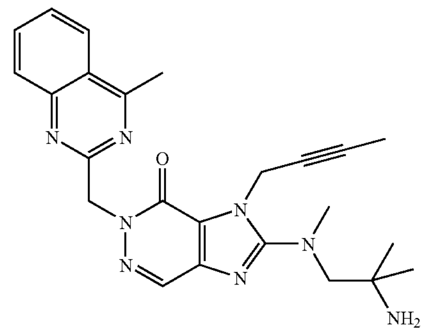 |
| (7) | 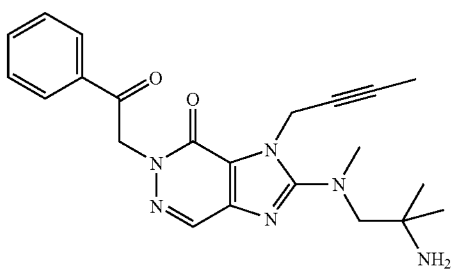 | (8) | 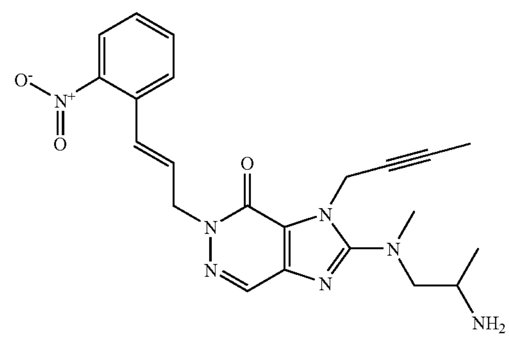 |
| (9) | 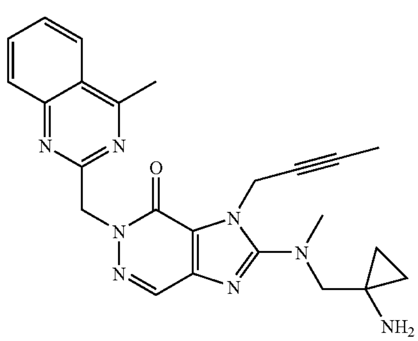 | (10) | 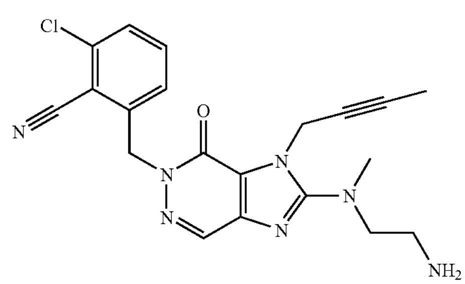 |
| (11) | 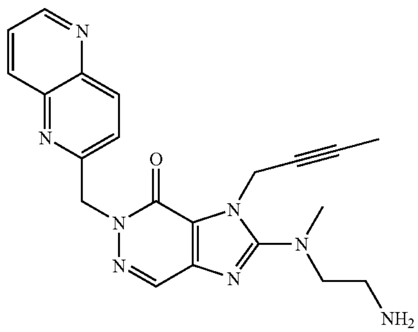 | (12) | 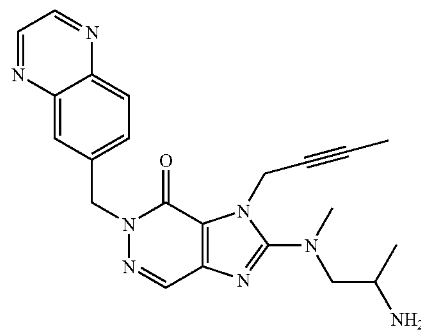 |

-continued
| Ex. | Structure | Ex. | structure |
|---|---|---|---|
| (13) | 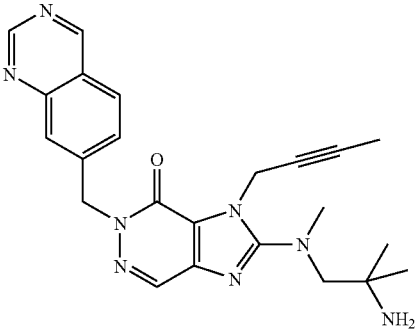 | (14) | 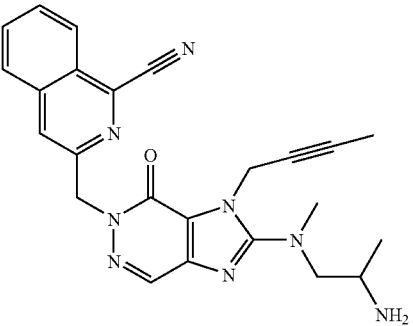 |
| (15) | 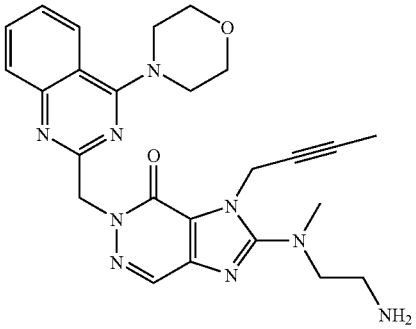 | (16) | 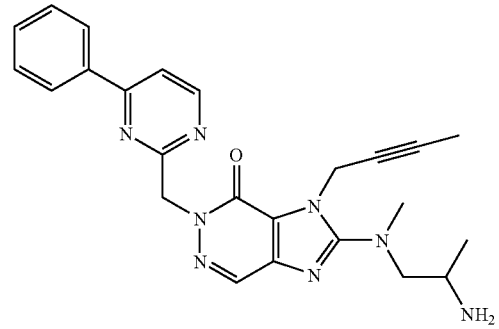 |
| (17) | 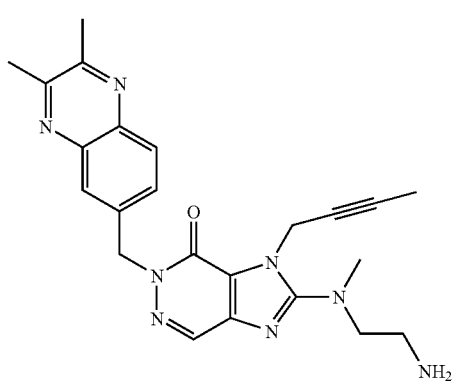 | (18) | 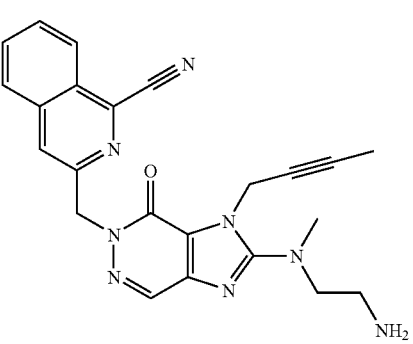 |
| (19) | 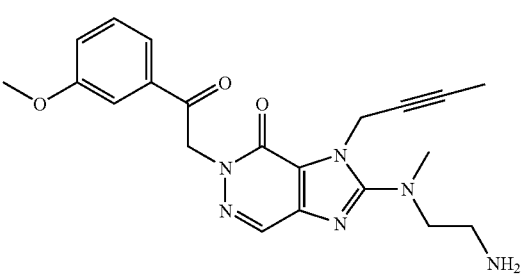 | (20) | 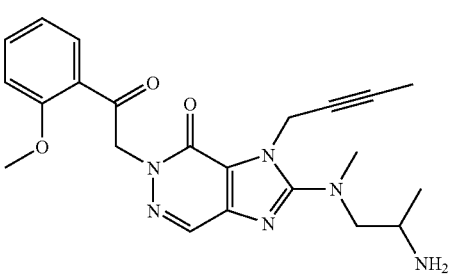 |

-continued

| Ex. | Structure | Ex. | structure |
|---|---|---|---|
| (21) | 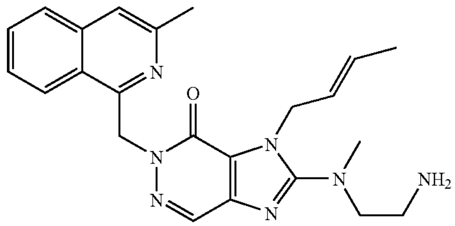 | (22) | 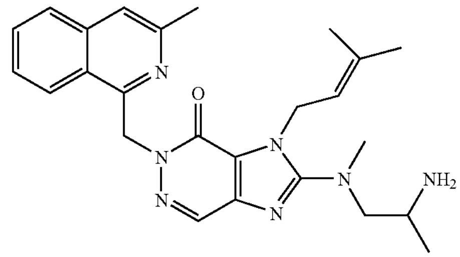 |
| (23) | 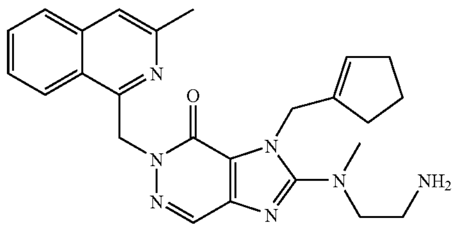 | (24) | 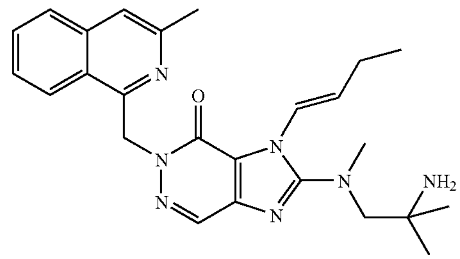 |
| (25) | 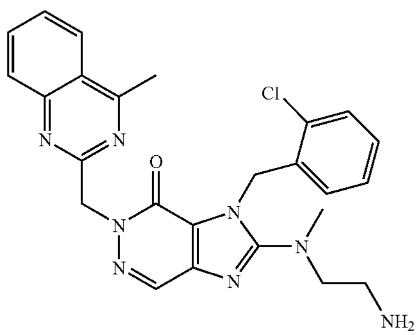 | (26) | 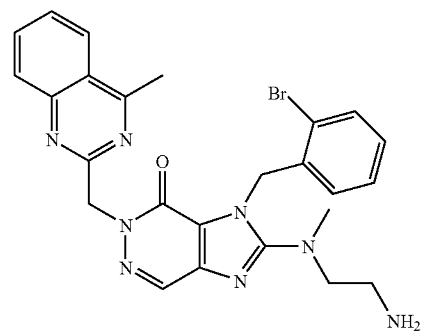 |
| (27) | 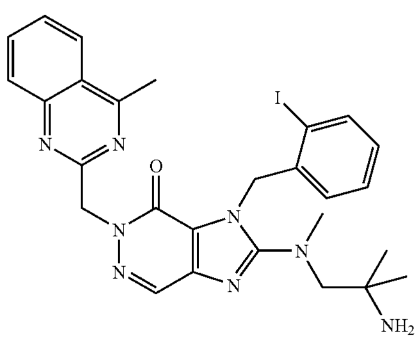 | (28) | 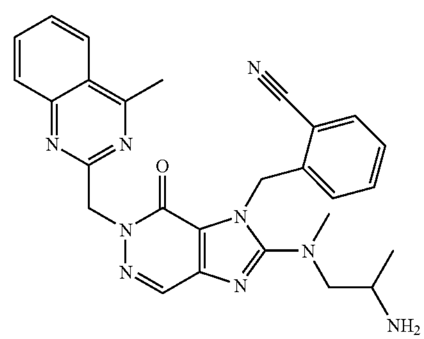 |
| (29) | 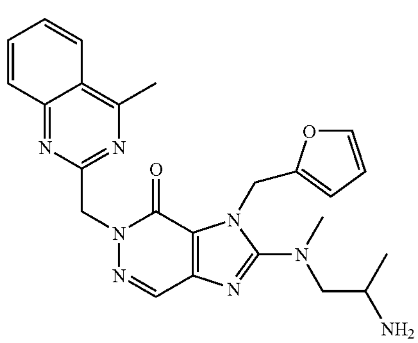 | (30) | 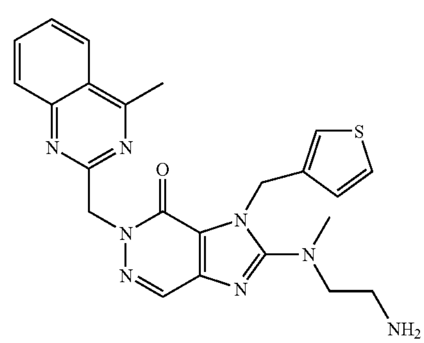 |

-continued
| Ex. | Structure | Ex. | structure |
|---|---|---|---|
| (31) | 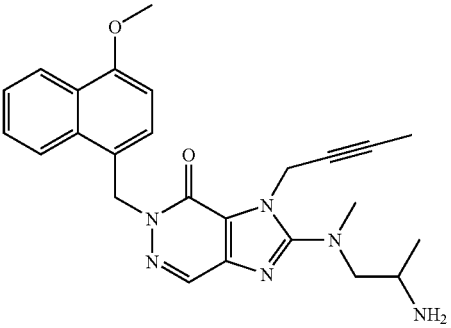 | (32) | 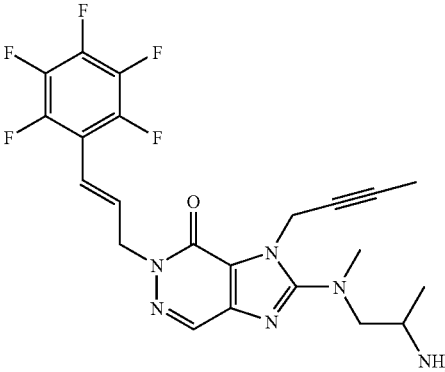 |
| (33) | 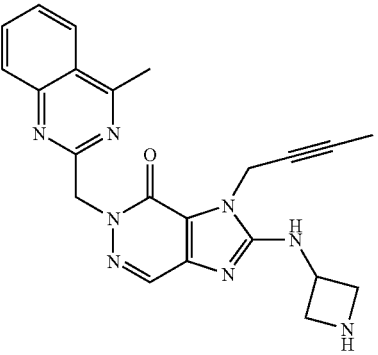 | (34) | 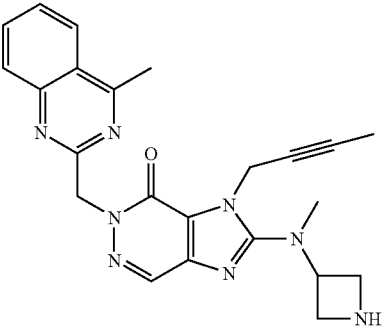 |
| (35) | 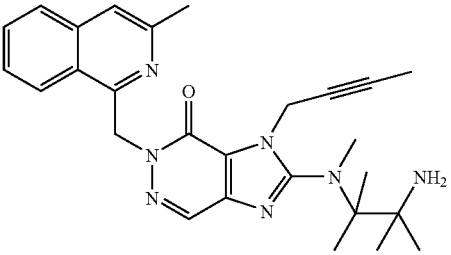 | (36) | 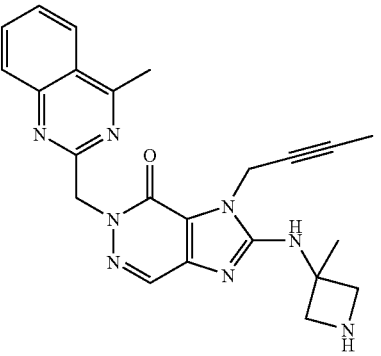 |
| (37) | 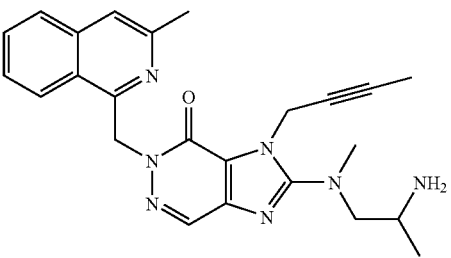 | (38) | 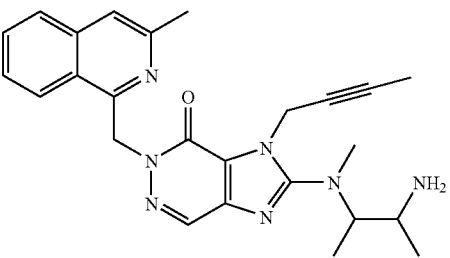 |

| Ex. | Structure | Ex. | structure |
|---|---|---|---|
| (39) | 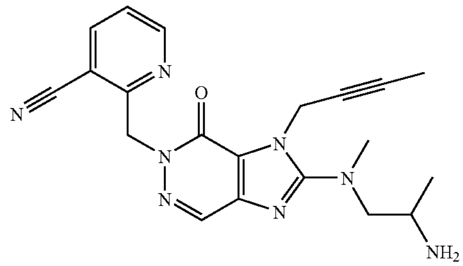 | (40) | 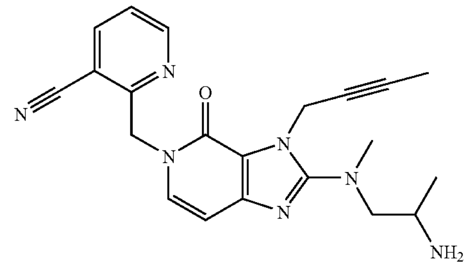 |
| (41) | 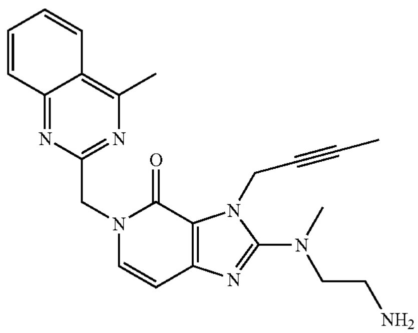 | (42) | 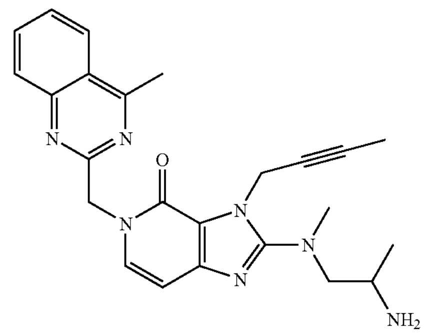 |
| (43) | 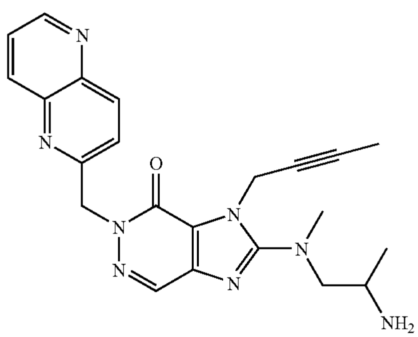 | (44) | 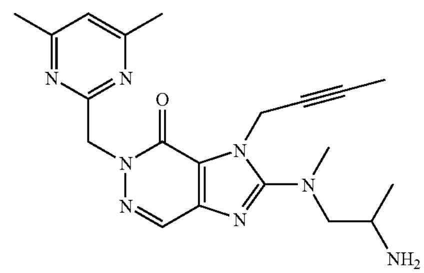 |

EXAMPLE A

Coated Tablets Containing 75 mg of Active Substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate.

This granulate is compressed in a tablet-making machine to form tablets of the desired shape.

weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE B

Tablets Containing 100 mg of Active Substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE C

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg die: 10 mm, flat

EXAMPLE D

Hard Gelatine Capsules Containing 150 mg of Active Substance

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE E

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE F

Suspension Containing 50 mg of Active Substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE G

Ampoules Containing 10 mg Active Substance

Composition:

| | |
|---|---|
| active substance | 10.0 mg |
| 0.01 N hydrochloric acid q.s. | ad 2.0 ml |
| double-distilled water | ad 100 ml |

Preparation:

The active substance is dissolved in the necessary amount of 0.01 N HCl, made isotonic with common salt, filtered sterile and transferred into 2 ml ampoules.

EXAMPLE H

Ampoules Containing 50 mg of Active Substance

Composition:

| | |
|---|---|
| active substance | 50.0 mg |
| 0.01 N hydrochloric acid q.s. | ad 10.0 ml |
| double-distilled water | ad 10.0 ml |

Preparation:

The active substance is dissolved in the necessary amount of 0.01 N HCl, made isotonic with common salt, filtered sterile and transferred into 10 ml ampoules.

We claim:

1. Compounds of formula I

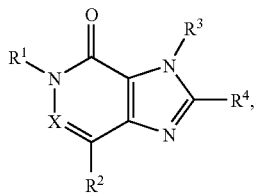

(I)

wherein
$R^1$ denotes an arylmethyl or arylethyl group,
a heteroarylmethyl or heteroarylethyl group,
an arylcarbonylmethyl group,
a heteroarylcarbonylmethyl group or
an arylprop-2-enyl or heteroarylprop-2-enyl group, wherein the propenyl chain may be substituted by 1 to 4 fluorine atoms or a cyano, $C_{1-3}$-alkyloxy-carbonyl or nitro group,
X denotes a nitrogen atom,
$R^2$ denotes a hydrogen atom,
a $C_{1-6}$-alkyl group,
an aryl or heteroaryl group,
a $C_{1-6}$-alkyl group substituted by a group $R_a$, where
$R_a$ denotes a $C_{3-7}$-cycloalkyl group wherein one or two methylene groups may each be replaced independently of one another by an oxygen or sulphur atom, by an —NH— or —N($C_{1-3}$-alkyl)- group or by a carbonyl, sulphinyl or sulphonyl group,
or a trifluoromethyl, aryl, heteroaryl, cyano, carboxy, $C_{1-3}$-alkoxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, arylcarbonyl, heteroarylcarbonyl, $C_{1-3}$-alkylsulphinyl, $C_{1-3}$-alkylsulphonyl, hydroxy, $C_{1-3}$-alkoxy, $C_{1-3}$-alkylsulphanyl, amino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group,
a trifluoromethyl, carboxy, $C_{1-4}$-alkoxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-3}$-alkyl)-piperazin-1-ylcarbonyl, arylcarbonyl, heteroarylcarbonyl, $C_{1-3}$-alkylsulphinyl, $C_{1-3}$-alkylsulphonyl,
$C_{1-4}$-alkoxy, $C_{1-4}$-alkylsulphanyl, amino, $C_{1-3}$-alkylamino or di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group,
a $C_{3-7}$-cycloalkyl group wherein one or two methylene groups independently of one another may each be replaced by an oxygen or sulphur atom, by an —NH— or N($C_{1-3}$-alkyl)- group, or by a carbonyl, sulphinyl or sulphonyl group, or
a $C_{3-6}$-alkenyl or $C_{3-6}$-alkynyl group,
$R^3$ denotes a $C_{5-7}$-cycloalkenylmethyl group optionally substituted by a $C_{1-3}$-alkyl group,
an arylmethyl or heteroarylmethyl group,
a straight-chain or branched $C_{2-8}$-alkenyl group which may be substituted by 1 to 15 fluorine atoms or a cyano, nitro or $C_{1-3}$-alkoxy-carbonyl group,
or a straight-chain or branched $C_{3-8}$-alkynyl group which may be substituted by 1 to 9 fluorine atoms or a cyano, nitro or $C_{1-3}$-alkoxy-carbonyl group,
and
$R^4$ denotes an amino group substituted by the groups $R^{15}$ and $R^{16}$ wherein
$R^{15}$ denotes a hydrogen atom, a $C_{1-6}$-alkyl, $C_{3-6}$-cycloalkyl, $C_{3-6}$-cycloalkyl-$C_{1-3}$-alkyl, aryl or aryl-$C_{1-3}$-alkyl group and
$R^{16}$ denotes a $R^{17}$-$C_{2-3}$-alkyl group, while the $C_{2-3}$-alkyl moiety is straight-chain and may be substituted by 1 to 4 $C_{1-3}$-alkyl groups, which may be identical or different, and
$R^{17}$ denotes an amino or $C_{1-3}$-alkylamino group,
an amino group substituted by the groups $R^{15}$ and $R^{18}$ wherein
$R^{15}$ is as hereinbefore defined and $R^{18}$ denotes a $C_{3-10}$-cycloalkyl-$C_{1-2}$-alkyl-group substituted in the 1 position of the cycloalkyl group by $R^{19}$ or a $C_{3-10}$-cyclo-alkyl group substituted in 1 or 2 position by a $R^{19}$-$C_{1-2}$-alkyl- group, while $R^{19}$ denotes an amino or $C_{1-3}$-alkylamino group,
an amino group substituted by the groups $R^{15}$ and $R^{20}$ wherein
$R^{15}$ is as hereinbefore defined and $R^{20}$ denotes a $C_4$- or $C_{8-10}$-cycloalkyl group wherein a methylene group from position 3 onwards of the $C_4$- or $C_{8-10}$-cycloalkyl group is replaced by an —NH— group,
or an amino group substituted by the groups $R^{15}$ and $R^{21}$ wherein
$R^{15}$ is as hereinbefore defined and $R^{21}$ denotes a $C_{3-4}$- or $C_{8-10}$-cycloalkyl group substituted in the 2 or 3 position by an amino or $C_{1-3}$-alkylamino group,
while the above-mentioned groups $R^{18}$, $R^{20}$ and $R^{21}$ may be mono- or disubstituted by $R_b$, the substituents may be identical or different and $R_b$ denotes a fluorine atom, a $C_{1-3}$-alkyl, trifluoromethyl, cyano, amino, $C_{1-3}$-alkylamino, hydroxy or $C_{1-3}$-alkyloxy group, and wherein one or two methylene groups of the cycloalkyl group independently of one another may each be replaced by an oxygen or sulphur atom or by an —NH— or N($C_{1-3}$-alkyl)- group, or by a carbonyl, sulphinyl or sulphonyl group,
while by the aryl groups mentioned in the definition of the above groups are meant phenyl or naphthyl groups, which may be mono-, di- or trisubstituted independently of one another by $R_h$, while the substituents may be identical or different and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, morpholinyl, hydroxy, $C_{1-3}$-alkyloxy, difluoromethoxy or trifluoromethoxy group, and wherein additionally each hydrogen atom may be replaced by a fluorine atom, by the heteroaryl groups mentioned in the definition of the above-mentioned groups is meant a pyrrolyl, furanyl, thienyl, pyridyl, indolyl, benzofuranyl, benzothiophenyl, quinolinyl or isoquinolinyl group, or is meant a pyrrolyl, furanyl, thienyl or pyridyl group, wherein one or two methyne groups are replaced by nitrogen atoms, or is meant an indolyl, benzofuranyl, benzothiophenyl, quinolinyl or isoquinolinyl group, wherein one to three methyne groups are replaced by nitrogen atoms, and the above-mentioned heteroaryl groups may be mono- or disubstituted by $R_h$, while the substituents may be identical or different and $R_h$ is as hereinbefore defined, by the above-mentioned cycloalkyl groups as defined are meant both monocyclic and also polycyclic ring systems, while the polycyclic groups may be annelated, spiro-linked or bridged in structure, while, unless otherwise stated, the above-mentioned alkyl, alkenyl and alkynyl groups may be straight-chain or branched, while the carboxy groups mentioned in the definition of the above-mentioned groups may be replaced by a group which may be converted in vivo into a carboxy group or by a group which is negatively charged under physiological conditions, and the amino and imino groups mentionied in the definition of the above-mentioned groups may be substituted by a group which can be cleaved in vivo, the tautomers, enantiomers, diastereomers, the mixtures thereof, and the salts thereof.

2. Compounds of formula I according to claim 1, wherein $R^1$ and $R^4$ are defined as mentioned in claim 1, X denotes a nitrogen atom, $R^2$ denotes a hydrogen atom, a $C_{1-4}$alkyl, $C_{3-6}$-cycloalkyl or phenyl group and $R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl, methoxybenzyl or cyanobenzyl group, the enantiomers, the diastereomers, the mixtures thereof and the salts thereof.

3. Compounds of formula I according to claim 2, wherein $R^1$ denotes a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, naphthyridinylmethyl or benzotriazolylmethyl group which may be substituted in each case by one or two fluorine, chlorine, bromine atoms or one or two cyano, nitro, amino, $C_{1-3}$-alkyl, $C_{1-3}$-alkyloxy and morpholinyl groups, while the substituents are identical or different, X denotes a nitrogen atom, $R^2$ denotes a hydrogen atom, $R^3$ denotes a 1-buten-1-yl, 2-buten-1-yl, 2-butyn-1-yl, cyclopent-1-enyl-methyl, furanylmethyl, thienylmethyl, chlorobenzyl, bromobenzyl, iodobenzyl or cyanobenzyl group and $R^4$ denotes an N-(2-aminoethyl)-N-methyl-amino group wherein the ethyl group may be substituted by 1 to 4 methyl groups, the tautomers, the mixtures thereof and the salts thereof.

4. Compounds of formula I according to claim 3, wherein $R^1$ denotes a isoquinolinylmethyl, quinazolinylmethyl or benzyl group which may be substituted by a methyl or cyano group, X denotes a nitrogen atom, $R^2$ denotes a hydrogen atom, $R^3$ denotes a 2-butyn-1-yl group and $R^3$ denotes an N-(2-aminoethyl)-N-methyl-amino, N-(2-aminopropyl)-N-methyl-amino or N-(2-amino-2-methylpropyl)-N-methyl-amino group, the tautomers and the salts thereof.

5. The following compounds of formula I according to claim 1:

(a) 2-[N-(2-aminoethyl)-N-methyl-amino]-3-(2-butyn-1-yl)-5-[(4-methyl-quinazolin-2-yl)methyl]-3,5-dihydro-imidazo[4,5-d]pyridazin-4-one (b) 2-[N-(2-aminoethyl)-N-methyl-amino]-3-(2-butyn-1-yl)-5-[(3-methyl-isoquinolin-1-yl)methyl]-3,5-dihydro-imidazo[4,5-d]pyridazin-4-one (c) (S)-2-[N-(2-aminopropyl)-N-methyl-amino]-3-(2-butyn-1-yl)-5-(2-cyanophenyl-methyl)-3,5-dihydro-imidazo[4,5-d]pyridazin-4-one (d) 2-[N-(2-amino-2-methyl propyl)-N-methyl-amino]-3-(2-butyn-1-yl )-5-(2-cyanophenylmethyl) -3,5-dihydro-imidazo[4,5-d]pyridazin-4-one (e) (S)-2-[N-(2-aminopropyl)-N-methyl-amino]-3-(2-butyn-1-yl)-5-[(4-methyl-quinazolin-2-yl)methyl]-3,5-dihydro-imidazo[4,5-d]pyridazin-4-one (f) (S)-2-[N-(2-amino-propyl )-N-methyl-amino]-3-(2-butyn- I -yl)-5-(4-cyano-isoquinolin-3-ylmethyl) -3,5-dihydro-imidazo[4,5-d]pyridazin-4-one as well as the tautomers and the salts thereof.

6. A pharmaceutical composition comprising the compound according to claim 1 or a physiologically acceptable salt thereof together with one or more inert carriers and/or diluents.

7. Process for preparing the compounds of formula I according to claim 1, the process comprising a) providing a compound of general formula II

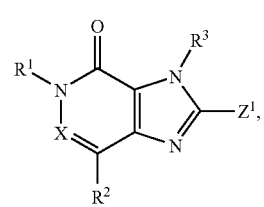

(II)

wherein $R^1$ to $R^3$ and X are defined as mentioned in claim 1 and $Z^1$ denotes a leaving group such as a halogen atom, a substituted hydroxy, mercapto, sulphinyl, sulphonyl or sulphonyloxy group, and b) reacting the compound of general formula II with $R^4$-H or salts thereof, where $R^4$ is defined as in claim 1.

8. Process for preparing the compounds of formula I according to claim 1, the process comprising
a) deprotecting a compound of formula III

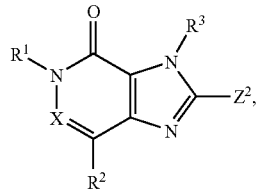

(III)

wherein $R^1$, $R^2$, $R^3$ and X are defined as mentioned in claim 1 and $Z^2$ denotes one of the groups mentioned for $R^4$ in claim 1 that contains an amino group not directly linked to the basic imidazopyridazinone structure, and wherein said amino group not directly linked to the basic imidazopyridazinone structure is protected by a tertbutyloxycarbonyl group.

9. The process according to claim 7 further comprising:
cleaving any protecting groups used during the reaction,
resolving the compounds of formula I thus obtained into their enantiomers or diastereomers and
converting the compounds of formula I thus obtained into their salts with inorganic or organic acids or bases.

10. The process according to claim 8 further comprising:
cleaving any protecting groups used during the reaction,
resolving the compounds of formula I thus obtained into their enantiomers or diastereomers and
converting the compounds of formula I thus obtained into their salts with inorganic or organic acids or bases.

* * * * *